United States Patent [19]
Weber

[11] Patent Number: 6,150,347
[45] Date of Patent: Nov. 21, 2000

[54] USE OF ALDOSTERONE ANTAGONISTS TO INHIBIT MYOCARDIAL FIBROSIS

[75] Inventor: Karl T. Weber, Columbia, Mo.

[73] Assignee: The Curators of the University of Missouri, Columbia, Mo.

[21] Appl. No.: 09/281,442

[22] Filed: Mar. 29, 1999

Related U.S. Application Data

[63] Continuation-in-part of application No. 07/871,390, Apr. 21, 1992, abandoned.

[51] Int. Cl.$^7$ .................................................. A61K 31/585
[52] U.S. Cl. .............................................................. 514/175
[58] Field of Search ............................................ 514/175

[56] References Cited

U.S. PATENT DOCUMENTS

| | | |
|---|---|---|
| 3,013,012 | 12/1961 | Cella, et al. . |
| 4,003,996 | 1/1977 | Pappo et al. . |
| 4,081,538 | 3/1978 | Ulick . |
| 4,559,332 | 12/1985 | Grob et al. . |
| 5,529,992 | 6/1996 | Weber . |
| 5,668,124 | 9/1997 | Weber . |
| 5,668,125 | 9/1997 | Weber . |

OTHER PUBLICATIONS

K. Weber, et al., "Myocardial Fibrosis, Aldosterone, and Antialdosterone Therapy: Evolving Concepts in the Management of Congestive Heart Failure," Copyrighted 1991 by G.D. Searle & Company, pp. 1–32.

"Highlights Report #1," *The XIIIth Congress of the European Society of Cardiology* (Amsterdam, The Netherlands), Aug. 1991, pp. 1–4.

C. G. Brilla, et al., "Anti–Aldosterone Treatment and the Prevention of Myocardial Fibrosis in Primary and Secondary Hyperaldosteronism," *Journal of Molecular Cellular Cardiology*, vol. 25, 1993, pp. 563–575.

C.G. Brilla et al., "Reactive and Reparative Myocardial Fibrosis in Arterial Hypertension in the Rat," *Cardiovascular Research*, No. 26, vol. 7, Jul. 1992, pp. 671–677.

K. Weber et al., "Factors Associated with Reactive and Reparative Fibrosis of the Myocardium," *4th Gargellen Conference on Cellular and Molecular Alterations in Failing Human Heart, Gargellen, Austria, Basic Res. Cardiol.* 87 (Suppl 1), 1992, pp. 291–301.

K. Weber et al., "Myocardial Fibrosis: Role of Ventricular Systolic Pressure, Arterial Hypertension, and Circulating Hormones," *6th Erwin Riesch Symposium, Feudenstadt, Germany* Oct. 11–14, 1990, Basic Res Cardiol. 86 (Suppl. 3), 1991 pp. 25–31.

Brilla et al., "Prevention of Myocardial Fibrosis in Hypertension: Role of Fibroblast Corticoid Receptors and Spironolactone," *75th Annual Meeting of Federation of American Societies for Experimental Biology, Atlanta, Georgia*, Apr. 21–25, 1991. FASEB (AM SOX EXPO Biol) No. 5, 5136.

Weber et al., "Myocardial Fibrosis: Role of Angiotensin II and Aldosterone," *Basic Research in Cardiology* 88 (Suppl. 1), 1993, pp. 107–124.

Weber et al., "Myocardial Fibrosis: Functional Significance and Regulatory Factors," *Cardiovascular Research* vol. 27, No. 3, 1993, pp. 341–348.

Weber et al., "Prevention of Myocardial Fibrosis in Hypertension: Anti–Fibrotic Effects in Spironolactone," *European Heart Journal*, vol. 12, 1991, 1961, p. 362.

C. G. Brilla et al., "Myocardial Collagen Matrix Remodelling in Arterial Hypertension," *European Heart Journal*, No. 13, Suppl. D, 1992, pp. 24–32.

K. Weber et al., "Myocardial Fibrosis and the Concepts of Cardioprotection and Cardioreparation," *Journal of Hypertension*, No. 10, (Suppl. 5), 1992, pp. S87–S94.

K. Weber, et al., Glucocorticoids and Mineralocorticoids: Antifibrotic and Profibrotic Components of Wound Healing, *Journal of Laboratory and Clinical Medicine*, vol. 120, No. 1, 1992, pp. 22–29.

K. Weber et al., "Myocardial Fibrosis and Elevations in Plasma Aldosterone in Arterial Hypertension," *Aldosterone: Fundamental Aspects*, vol. 215, 1991, pp. 117–120.

K. Weber, et al., "Pathological Hypertrophy and Cardiac Interstitium: Fibrosis and Renin–Angiotensin–Aldosterone System," *Circulation* 83:1849, Feb. 5, 1991, pp. 1849–1865.

D. Klug, et al., "Role of Mechanical and Hormonal Factors in Cardiac Remodeling and the Biologic Limits of Myocardial Adaptation," A Symposium: Aldosterone and Antialdosterone Therapy in Cardiovascular Disease, *The American Journal of Cardiology*, vol. 71, Jan. 21, 1993, pp. 46A–54A.

C. Brilla, et al., "Antifibrotic Effects of Spironolactone in Preventing Myocardial Fibrosis in Systemic Arterial Hypertension," A Symposium: Aldosterone and Antialdosterone Therapy in Cardiovascular Disease, *The American Journal of Cardiology*, vol. 71, Jan. 21, 1993, pp. 12A–16A.

K. Weber, et al., "Aldosterone and Myocardial Fibrosis in the Rat with Renovascular Hypertension or Hyperaldosteronism," Univ. of Mo., Division of Cardiology, Dec. 12, 1990, 2 pages.

K. Weber, et al., "Myocardial Remodeling and Pathologic Hypertrophy," *Hospital Practice*, Apr. 15, 1991, pp. 73–80.

K. Weber, et al., "Aldosterone and Antialdosterone Therapy in Congestive Heart Failure," A Symposium: Aldosterone and Antialdosterone Therapy, *American Journal of Cardiology*, vol. 71, 1993, pp. 3A–11A.

C.G. Brilla, et al., "Aldosterone–Mediated Stimulation of Collagen Synthesis in Cultured Cardiac Fibroblasts," *XIVth Congress of the European Society of Cardiology*, Aug. 30–Sep. 2, 1992, p. 1421.

(List continued on next page.)

*Primary Examiner*—Rebecca Cook
*Attorney, Agent, or Firm*—Shook, Hardy & Bacon LLP

[57] ABSTRACT

This invention discloses a method of using an aldosterone antagonist such as spironolactone, at a dosage which does not disrupt a patient's normal electrolyte and water-retention balance, to inhibit myocardial fibrosis, including left ventricular hypertrophy (LVH).

20 Claims, No Drawings

OTHER PUBLICATIONS

C.G. Brilla, et al., "Collagen Metabolism in Cultured Adult Rat Cardiac Fibroblasts: Response to Angiotensin II and Aldosterone,"*Journal of Molecular and Cellular Cardiology,* vol. 26, No. 7, Jul. 1994, pp. 809–820.

Gduardo, et al., "Endothelial Cell Induced Modulation of Cardiac Fibroblast Collagen Metabolism," *Cardiovascular Research,* vol. 27, No. 6, 1993, pp. 1004–1008.

Takeda, et al., "Regulation of Aldosterone Synthase in Human Vascular Endothelial Cells by Angiotensin II and Adreno–corticotropin," *Journal of Clinical Endocrinology,* vol. 81, No. 8, 1996, pp. 2797–2800.

Silvestre, et al., "Myocardial Production of Aldosterone and Corticosterone in the Rat," *The Journal of Biological Chemistry,* vol. 273, No. 9, Feb. 27, 1998, pp. 4883–4891.

C. Brilla, et al., "Angiotensin II–Mediated Aldosterone Synthesis in Aortic Endothelial Cells," *Circulation,* vol. 86, No. 4, Suppl. 1, 1992, p. I90.

E. Guarda, et al., "Endothelin–1 Elicits Aldosterone (Aldo) Release from Cultured Endothelial Cells," 1992 Meeting of the Federation of American Societies for Experimental Biology (FASEB), *Fed Am Soc Exp Biol Journal,* vol. 6, No. 1, 1992, p. 1811.

P. Greenberger, et al., "Readministration of Spironolactone–Intolerant Patient,"*NER Allergy Proc.,* undated, pp. 343–345.

C.G. Brilla, et al., "Renin–angiotensin System and Myocardial Fibrosis in Hypertension: Regulation of the Myocardial Collagen Matrix," *European Heart Journal,* vol. 14 (Suppl. J), 1993, pp. 57–61.

K. Weber, et al., "Regulatory Mechanisms of Myocardial Hypertrophy and Fibrosis: Results of in vivo Studies," *Cardiology,* vol. 81 (4–5), 1992, pp. 266–273.

Y. Sun, et al., "Myocardial Fibrosis: Metabolically Active Tissue," *Clinical Research,* vol. 41, No. 3, Oct. 1993, p. 660.

C.G. Brilla, et al., "Renin–Angiotensin System and Myocardial Collagen Matrix Remodeling in Hypertensive Heart Disease: In Vivo and in Vitro Studies on Collagen Matrix Regulation," Clinical Investigator, No. 71, 1993, pp. S35–S41.

C.G. Brilla, et al., "Inhibition of Collagenase Activity in Cultured Cardiac Fibroblasts by Angiotensin II," *XIVth Congress of the European Society of Cardiology, Barcelona, Spain, European Heart Journal,* No. 13 (Abstr. Suppl.), Aug. 30–Sep. 1, 1992, p. P700.

G. Zhou, et al., "Angiotensin II–Mediated Stimulation of Collagen Synthesis in Cultured Cardiac Fibroblasts," 1992 Meeting of Federation of American Societies for Experimental Biology, (FASEB), Part II, Anaheim, CA, *Fed Am Soc Exp Biol,* Journal 6 (5), Apr. 5–9, 1992, A1914, #5661.

L. Matsubara, "Angiotensin II–Mediated Inhibition of Collagenase Activity in Cultured Cardiac Fibroblasts," 1992 Meeting of the Federation of American Societies for Experimental Biology (FASEB), Part I, Anaheim, CA, *Fed Am Soc Exp Biol,* Journal 6 (4), Apr. 5–9, 1992, A941, #30.

K. Weber, et al., "Cardiac Interstitium: Extracellular Space of the Myocardium," *The Heart and Cardiovascular System Scientific Foundations,* Second Edition, vols. 1 and 2, 1991, pp. 1465–1480.

K. Weber, et al., "Cardioreparation with Lisinopril in the Management of Hypertension and Heart Failure," *Cardiology,* vol. 79 (Suppl 1), Jul. 1991, pp. 62–73.

C. Brilla, et al., "Impaired Diastolic Function and Coronary Reserve in Genetic Hypertension Role of Interstitial Fibrosis and Medial Thickening of Intramyocardial Coronary Arteries," *Circulation Research,* vol. 69 (1), Jul. 1991, pp. 107–115.

C. Brilla, et al., "Cardioreparative Effects of Lisinopril in Rats with Genetic Hypertension and Left Ventricular Hypertrophy," *Circulation,* vol. 83, No. 5, Jul. 1991, pp. 1771–1779.

J. Jalil et al., "Coronary Vascular Remodeling and Myocardial Fibrosis in the Rat with Renovascular Hypertension Response to Captopril," *American Journal of Hypertension,* vol. 4, No. 1, Part 1, Jan. 1991, pp. 51–55.

K. Weber, et al., "Fibrillar Collagen and Remodeling of Dilated Canine Left Ventricle," *Circulation,* vol. 82, No. 4, Oct. 1990, pp. 1387–1401.

K. Weber, et al., "Myocardial Fibrosis and Pathologic Hypertrophy in the Rat with Renovascular Hypertension," Symposium on Arterial Hypertension: Cardiac Hypertrophy and Failure, Dusseldorf, Germany, Jun. 8–10, 1989, *American Journal of Cardiology,* vol. 65, No. 14, Apr. 3, 1990, pp. 1G–7G.

C. Brilla, et al., "Cardioprotective Effects of Lisinopril in Rats with Genetic Hypertension," 74th Annual Meeting of the Federation of American Societies for Experimental Biology Part II, Washington, D.C., Apr. 1–5, 1990, *Fed Am Soc Exp Biol,* Journal 4, No. 4, 1990, p. A992.

K. Weber et al., "Myocardial Collagen Remodeling in Pressure Overload Hypertrophy: A Case for Interstitial Heart Disease," *Am J Hypertension,* vol. 2, No. 12, Part 1, Dec. 1989, pp. 931–940.

R. Pick, et al., "Myocardial Fibrosis in Non–Humane Primate with Pressure Overload Hypertrophy," *American Journal of Pathology,* vol. 135, No. 5, Nov. 1989, pp. 771–781.

J. Jalil, et al., "Captopril Pretreatment and Myocardial Fibrosis and Stiffness in Renovascular Hypertensive Rats," 38th Annual Scientific Session of the American College of Cardiology, Anaheim, CA, *Journal American College of Cardiology,* vol. 13, No. 2, Suppl. A, Feb. 1989, pp. 82A.

C. Brilla, et al., "Advanced Hypertensive Heart Disease in Spontaneously Hypertensive Rats: Lisinopril–Mediated Regression of Myocardial Fibrosis," Clinical Research, vol. 40, No. 3, Oct. 1992, p. 685A.

C. Brilla, et al., "Advanced Hypertensive Heart Disease in SHR: Lisinopril–Mediated Regression of Myocardial Fibrosis," Abstracts from the 65th Scientific Sessions, *Supplement to Circulation,* I–329, 1309, 1991–1992, 2 pages.

T. Risler, et al., "Influence of Short Versus Long Acting ACE Inhibitors on Neurohormonal Regulation in Severe Chronic Heart Failure," Proceedings of the Fourth International Conference on Diuretics, Boca Raton, Florida, Oct. 11–16, 1992, *International Congress* Series No. 1023, 1993, pp. 587–590.

K. Weber, et al., Structural Basis for Pathologic Left Ventricular Hypertrophy,: *Clinical Cardiology,* vol. 16, No. 5, (Suppl. 1), May 1993, pp. II10–II14.

C. Brilla, "Angiotensin II Type 2 Receptor–Mediated Stimulation of Collagen Synthesis in Human Cardiac Fibroblasts," *Circulation,* vol. 86, No. 4, Suppl. 1, 1992, p. I89.

K. Swedberg, et al., "Hormones Regulating Cardiovascular Function in Patients with Severe Congestive Heart Failure and Their Relation to Mortality," *Circulation,* vol. 82, No. 5, Nov. 1990, pp. 1730–1736.

C.G. Brilla, et al., "Regression of Myocardial Fibrosis in Hypertensive Heart Disease," *European Heart Journal*, vol. 12, 1991, 1274, p. 242.

K. Weber, et al., "Remodeling and Reparation of the Cardiovascular System," *Journal of the American College of Cardiology*, vol. 20, No. 1, 1992, pp. 3–16.

The RALES Investigators, "Effectiveness of Spironolactone Added to an Angiotensin–Converting Enzyme Inhibitor and a Loop Diuretic for Severe Chronic Congestive Heart Failure (The Randomized Aldactone Evaluation Study [RALES])," *The American Journal of Cardiology*, vol. 78, Oct. 15, 1996, pp. 902–907.

C. G. Brilla, et al., "Mineralocorticoid Excess, Dietary Sodium, and Myocardial Fibrosis," *Journal of Laboratory Clinical Medicine*, vol. 120, No. 6, Dec. 1992, pp. 893–901.

A. Diaz–Arias, et al., "Reactive Fibrosis of Coronary and Systemic Circulations in Adrenal Adenoma," Meeting of the Federation of American Societies for Experimental Biology, (FASEB), Part II, Anaheim, CA, *Fed Am Soc Exp Biol*, Journal 6(5), Apr. 5–9, 1992, A1915.

C.G. Brilla, et al., "Aldosterone and Collagen Synthesis in Cultured Adult Rat Cardiac Fibroblasts," 1992 Meeting of Federation of American Societies for Experimental Biology, (FASEB), Part II, Anaheim, CA, *Fed Am Soc Exp Biol*, Journal 6 (5), Apr. 5–9, 1992, A1914.

H. Reddy, et al., "Enhanced Coronary Macromolecular Permeability Role of Angiotensin II Aldosterone and Hypertension," 64th Scientific Sessions of the American Heart Association, Anaheim, CA, *Circulation 84*(4 Suppl.), Nov. 11–14, 1991, II557, 2 pages.

A. Diaz–Arias, et al., "Reactive Fibrosis of Coronary and Systemic Circulations in Adrenal Adenoma," Joint Meeting of the Central Society for Clinical Research, Midwest Section American Federation for Clinical Research, Midwest Society for Pediatric Research and Central Region Society for Investigative Dermatology, Chicago, IL, *Clinical Research*, vol. 39, No. 3, Nov. 6–8, 1991, 773A.

D. Chapman, et al., "Regulation of Fibrillar Collagen Types I and II and Basement Membrane Type IV Collagen Gene Expression in Pressure Overloaded Rat Myocardium," *Circulation Research*, vol. 67, No. 4, Oct. 1990, pp. 787–794.

M. Silver, et al., "Reactive and Reparative Fibrillar Collagen Remodelling in the Hypertrophied Rat Left Ventricle: Two Experimental Models of Myocardial Fibrosis," *Cardiovascular Research*, vol. 24, No. 9, Mar. 21, 1990, pp. 741–747.

M. Silver, et al., "Heterogeneous Patterns of Experimental Fibrosis in the Hypertrophied Rat Ventricle," National Meeting of the American Federation for Clinical Research, Washington, *Clinical Research*, vol. 38, No. 2, Apr. 1990, p. 543A.

C. Brilla, et al., "Myocardial Fibrosis in Either Renovascular or Mineralocorticoid Hypertension," National Meeting of the American Society for Clinical Investigation, Washington, D.C., May 4–7, 1990, *Clinical Research*, vol. 38, No. 2, Apr. 1990, p. 588A.

G. Zhou, et al., "Angiotensin II and Aldosterone Regulate Collagen Metabolism of Cardiac Fibroblasts," *Clinical Research*, vol. 40, No. 3, Oct. 1992, p. 705A.

E. Guarda, et al., "Alteration of Cardiac Fibroblast Collagen Metabolism by Endothelin–1," *Clinical Research*, vol. 40, No. 3, Oct. 1992, p. 705A.

E. Guarda, et al., "Modulation of Cardiac Fibroblasts Collagen Metabolism by Endothelial Cells," *Clinical Research*, vol. 40, No. 3, Oct. 1992, p. 756A.

C.G. Brilla, et al., "Myocardial Fibrosis in Experimental Hypertension: Potential Role of Fibroblast Corticoid Receptors," *J. Hypertension*, vol. 8, No. 3 (Suppl), Jun. 1990, pS8.

C. Doering, et al., "Collagen Network Remodelling and Diastolic Stiffness of the Rat Left Ventricle with Pressure Overload Hypertrophy," *Cardiovascular Research*, vol. 22, Feb. 12, 1988, pp. 686–695.

C. Brilla, et al., "Remodeling of the Rat Right and Left Ventricles in Experimental Hypertension," *Circulation Research*, vol. 67, No. 6, Dec. 1990, pp. 1335–1364.

T. Andreoli, "Introduction: Modern Aspects of Congestive Heart Failure," *Hospital Practice*, Apr. 15, 1991, pp. 7–8.

K. Weber, et al., "Structural Remodeling of Myocardial Collagen in Systemic Hypertension: Functional Consequences and Potential Therapy," *Heart Failure*, Jul./Aug. 1990, pp. 129–137.

M. Agarwal, "Analysis of Mineralocorticoid Receptor in Rat Heart with the Aid of Two New Spirolactone Derivatives," *Biochemical Medicine and Metabolic Biology*, vol. 41, No. 1, Feb. 1989, pp. 36–45.

K. Weber, et al., "Angiotensin II, Aldosterone, and Connective tissue formation in the Cardiovascular System," *Univ. of Mo., Dept. of Cardiology*, circa 1992, 4 pages.

M. Gasparo, et al., "Three New Epoxy–Spirolactone Derivatives Characterization in Vivo and in Vitro," *Journal of Pharmacology and Experimental Therapeutics*, vol. 240, No. 2, Nov. 3, 1996, pp. 650–656.

Mack Publishing Company, "Remington's Pharmaceutical Sciences," *XIVth Edition*, 1975, pp. 867–868.

Bundesverband D. Pham. Ind. E.V. 'Rote Liste' 1987, Editio Cantor, Avlendorf/Wurtt, 3 pages.

K. Nickisch, et al., "Aldosterone Antagonists. 4. Synthesis and Activities of Steroidal 6, 6–Ethylene–15, 16–methylene 17–Spirolactones," *Journal of Medicinal Chemistry*, vol. 34, No. 8, 1991, pp. 2464–2468.

Agarwal, M.K. and Lazar, G., "Antimineralocorticoids," *Renal Physiol. Biochem*, 14: 217–223 (1991).

Barton, D.H.R., et al., "Improved Syntheses of Aldosterone," *J. Chem. Soc. Perkin Trans I*: 2243–2251 (1975).

Blitstein–Willinger, E., "The role of growth factors in would healing," *Skin Pharmacol.* 4: 175–182 (1991).

Hassager, C., et al., "Collagen synthesis in postmenopausal women during therapy with anabolic steriod or female sex hormones," *Metabolism 39*: 1167–1169 (1990).

Jalil, J.E., et al., "Structural v. contractile protein remodeling and myocardial stiffness in hyperthrophied rat left ventricle," *J. Mol. Cell Cardiol 20*: 1179–1187 (1988).

Jalil, J.E., et al., "Fibrillar collagen and myocardial stiffness in the intact hypertrophied rat left ventricle," *Circ. Res. 64*: 1041–1050 (1989).

Kornel, L., et al., "Arterial steroid receptors and their putative role in the mechanism of hypertension," *J. Steroid Biochem. 19*: 333–344 (1983).

Losert, W., et al., "Mespirenone and other 15,16–methylene–antagonists," *Drug Res. 36*: 1583–1600 (1986).

Luke, J.L., et al., "Sudden cardiac death during exercise in a weight lifter using anabolic steroids: Pathological and toxicological findings," *J. Forensic Sci. 35*: 1441–1447 (1990).

Meyer, W.J., and Nicholos, N.R., "Mineralocorticoid binding in cultured smooth muscle cells and fibroblasts from rat aorta," *J. Steroid Biochem. 14*: 1157–1168 (1981).

Miyano, M., "Synthesis of Aldosterone," *J. Org. Chem. 46*: 1846–1853 (1981).

Rothe, M., and Falanga, V., "Growth factors: Their biology and promise in dermatologic diseases and tissue repair," *Arch. Dermatol. 125*: 1390–1398 (1989).

Skelton, F.R., "The production of hypertension, nephrosclerosis and cardiac by methylandrostenediol treatment in the rat," *Endocrinology 53*: 492–505 (1953).

USE OF ALDOSTERONE ANTAGONISTS TO INHIBIT MYOCARDIAL FIBROSIS

RELATED APPLICATION

This application is a continuation-in-part of U.S. patent application Ser. No. 07/871,390, filed on Apr. 21, 1992 abandoned.

GOVERNMENT SUPPORT

This invention was supported in part by grant R01-31701 from the National Institutes of Health. Accordingly, the federal government has certain rights in this invention.

BACKGROUND OF THE INVENTION

This invention relates to drugs such as spironolactone which block the activity of the hormone aldosterone, and to the use of aldosterone-blocking drugs to prevent or treat myocardial fibrosis, a disease condition.

In a medical context, fibrosis refers the creation of fibrotic tissue (i.e., tissue characterized by an abnormally high quantity of fibrous material, primarily strands of collagen). In some situations, fibrosis is useful and necessary, such as in the healing of wounds, but in other situations, fibrosis can be harmful, especially when it interferes with the functioning of internal organs. As one example, liver cirrhosis is usually characterized by high levels of fibrosis. That condition, discussed in the above-cited parent application, Ser. No. 07/871,390, is not directly relevant to this invention.

This invention relates to the use of mineralocorticoid antagonists (such as spironolactone) in inhibiting myocardial fibrosis.

The correlation between mineralocorticoids and fibrosis was not recognized prior to the work of the Applicant. However, a great deal was known about mineralocorticoids and about fibrosis, as separate fields in medicine and physiology. Accordingly, the following sections provide background information on each of those topics.

Mineralocorticoids

The adrenal glands, which sit on top of the kidneys in the human body, are divided into two portions: the adrenal medulla (which secretes epinephrine and norepinephrine), and the adrenal cortex. The adrenal cortex secretes a number of hormones known as corticoids, which are divided into two categories. Glucocorticoids (primarily hydrocortisone, also known as cortisol) exert their primary effects on the metabolism of glucose and other carbohydrates; they can also secondarily retard wound healing, by interfering with inflammatory cell and fibrous tissue responses. The primary effects of mineralocorticoids (MC's) involve the retention of certain minerals, particularly sodium, and the elimination of potassium.

The most important and potent MC is aldosterone (ALDO); another naturally occurring MC which is less potent is deoxycorticosterone (DOC). If ALDO is present at abnormally high quantities (such as following hemorrhage, bodily injury, or sodium deprivation), the body will retain sodium and water, and will secrete potassium. This can be a beneficial short-term response to stress. However, chronic elevations of ALDO can be detrimental, such as in a patient with heart failure who is suffering from edema (fluid accumulation), or a patient with hypertension (high blood pressure). In patients with edema or hypertension, an excess of ALDO promotes salt and water retention and potassium loss, which are detrimental. Certain drugs, most notably spironolactone (discussed below), can be used to suppress activity of elevated circulating ALDO, or to suppress the synthesis of ALDO.

ALDO secretion is influenced by various signals involving adrenocorticotropin hormone (ACTH), melanocyte stimulating hormone, atrial natriuretic peptide, and plasma concentrations of sodium and potassium, and by a multi-step pathway called the renin-angiotensin-aldosterone (RAA) system. In response to certain signals which indicate low blood pressure, the kidneys secrete renin, which cleaves a precursor peptide called angiotensinogen to release a peptide having ten amino acid residues, called angiotensin I. This peptide is cleaved by another enzyme called angiotensin converting enzyme (ACE) to generate angiotensin II, which has eight amino acid residues. In addition to being a potent vasoconstrictor (which increases blood pressure), angiotensin II functions as a hormone to stimulate the release of ALDO by zona glomerulosa cells in the adrenal cortex. The RAA system is described in more detail in articles such as Weber and Brilla 1991 (full citations are provided below).

ALDO receptors (also called mineralocorticoid receptors (MCR or MinR, or mineralosteroid receptors) are proteins that initially reside in the cytoplasm of certain types of cells, such as smooth muscle cells and fibroblasts in the aorta (see, e.g., Meyer and Nichols 1981). When an ALDO receptor is activated by ALDO, the receptor/ALDO complex (or least some portion thereof) is transported into the cell nucleus, where it binds to nuclear chromatin and presumably causes an alteration in the transcription of genes that encode proteins which are involved in the retention of sodium and water by the body (see, e.g., Kornel et al 1983). For more information on ALDO receptors, see Agarwal and Lazar 1991 and additional references cited therein. Chemical methods of synthesizing aldosterone are described in articles such as Barton et al 1975 and Miyano 1981.

Fibrosis

Fibrosis (the generation of fibrotic tissue) is important in a number of processes in adult mammals. In some processes, such as wound healing, fibrosis is highly beneficial and essential to survival. When one or more blood vessels, which function as barriers to separate the intravascular and extracellular spaces, are cut or otherwise broken or disrupted, an orderly wound healing process is initiated. Certain types of blood cells such as platelets release fibrinogen, plasminogen, and fibronectin into the cellular interstitium; these molecules react with other molecules to generate an extravascular coagulation and the formation of a hydrophilic fibrin-fibronectin gel. Various growth factors are believed to orchestrate the subsequent entry of immune and inflammatory cells and fibroblasts into the gel and the formation of new blood vessels within its interstices.

During the early stages, the gel is considered granulomatous tissue. It is gradually resorbed and replaced by fibrous tissue. One of the important components of such tissue is collagen, a fibrous protein secreted by fibroblasts; it provides an intercellular lattice or matrix which anchors cells in position in cohesive tissue (such as muscle or blood vessels).

In addition to synthesizing and secreting collagen, fibroblasts also synthesize and secrete collagenase, an enzyme which digests collagen. In healthy tissue, the gradual cycle of collagen secretion and degradation helps ensure that the protein fibers and connective tissue remain flexible, elastic, and in a steady-state concentration.

If fibrosis occurs as a wound-healing process in response to injury, it is classified as "reparative" fibrosis. Similarly, if fibrosis is initiated in an internal organ in response to the necrosis of parenchymal cells (i.e., cells which are characteristic of that particular organ, as distinct from non-specific cells), the generation of fibrotic tissue constitutes reparative fibrosis. In either case, collagen accumulation and connective tissue formation usually resemble scar tissue.

In some situations which can generally be regarded as disease conditions, blood vessels can lose their integrity and become permeable to macromolecules, even in the absence of a cut or other injury. In such situations, fibrosis can arise which is unwanted and unnecessary; it resembles a wound healing response that has gone awry. In the absence of parenchymal cell loss, this type of fibrosis can be classified as a "reactive" fibrosis. If a sufficient quantity of unwanted fibrotic tissue is generated in an internal organ such as the heart, the fibrotic tissue can compromise or seriously damage the functioning of the organ.

Humans or animals that suffer from chronic hypertension or edema often are found, upon autopsy, to have heart muscle that suffers from a characteristic often referred to by pathologists as "tough beef." Instead of appearing pliable, elastic, and free of stranded material, like a fresh high-quality filet mignon, the heart muscle is riddled and interspersed with fibrotic strands which render the heart muscle stiff and unable to flex, move, and function with full efficiency. This condition is referred to as myocardial fibrosis when it involves heart muscle (in medicine, the prefix "myo" refers to muscle), or as cardiac fibrosis (which is somewhat broader, since it can also include fibrosis in coronary arteries).

Myocardial fibrosis can be generated in lab animals in any of several ways. Animals models which have been reported in the literature (e.g., Doering et al 1988 and Brilla et al 1990) involve: (1) renovascular hypertension (RHT), which can be induced by surgically placing a constricting band around a renal artery for a prolonged period (such as several weeks, in rats); and, (2) ALDO-induced hypertension, in which animals are administered ALDO (usually by means of a small osmotic pump implanted beneath the skin, which slowly releases ALDO over a period of weeks) while being fed a high-salt diet. Either of these interventions, discussed in more detail below, will provoke an unwanted myocardial fibrosis in a previously normal heart.

One of the main forms of myocardial fibrosis involves a condition known as "left ventricular hypertrophy," which is discussed at some length in Weber and Brilla 1991. The left ventricle is the largest pumping chamber of the heart; it pumps blood through the entire body and head, excluding the lungs (which receive blood from the right ventricle). "Hypertrophy" refers to a non-tumorous increase in the size of an organ or muscle, and in left ventricular hypertrophy (LVH), the muscular wall of the left ventricle becomes excessively large. LVH is the single most important risk factor associated with adverse myocardial events, including myocardial failure and sudden death.

In animal models, LVH can be induced (for the purpose of studying it) by various means that generate hypertension over a prolonged period of time. Such interventions include (1) surgically constricting an artery that supplies the kidneys; (2) feeding animals a high-sodium diet coupled with ALDO injections; and, (3) infrarenal aortic banding, which involves surgically clamping the abdominal aorta below the junction where the renal arteries branch off; this reduces blood flow to the legs and elevates blood pressure in the thoracic region. In many but not all cases, LVH is accompanied by fibrosis (see, e.g., Jalil et al 1988 and 1989).

Fibrosis has also been observed as a result of steroid use or abuse by humans, and steroid administration to lab animals; see, e.g., Skelton 1954, Hassager et al 1990, and Luke et al.

Most types of reactive fibrosis are initially characterized by "perivascular" fibrosis (i.e., fibrosis which is localized around blood vessels). As the process of fibrosis continues and fills the spaces between various types of cells, it can be characterized as an "interstitial" fibrosis.

Fibrosis is intimately related to collagen metabolism by fibroblast cells. In the repair of wounds or cell necrosis, the activity of fibroblasts in synthesizing fibrillar collagen and in secreting collagenase will have a major impact on whether the fibrous tissue component of the wound healing or tissue replacement response is appropriate and proceeds to a successful conclusion. In reactive fibrosis, the amount of undesired collagen deposition will also depend on the level of activity of the fibroblasts involved.

Various factors are known to regulate collagen metabolism and fibroblast growth, or both, and thereby govern collagen accumulation (see, e.g., Rothe and Falanga 1989). These include cytokines such as fibroblast growth factor, platelet derived growth factor and transforming growth factor-beta$_1$. Hormones are also involved, such as the above-mentioned glucocorticoids, which oppose various aspects of wound healing including inflammatory cell and fibrous tissue responses and which have antifibrotic properties relative to wound healing.

The processes of myocardial fibrosis, and the structure and arrangement of collagen fibers and cells in heart muscle, are described and illustrated in articles such as Weber and Brilla 1991. Articles which focus more specifically on the role of cytokines and other growth factors on wound healing include Blitstein-Willinger 1991 and Rothe and Falanga 1989.

Anti-Aldosterone Drugs

A number of drugs have been identified which can inhibit the activity of ALDO in the body, including spirolactones. The term "spirolactone" indicates that a lactone ring (i.e., a cyclic ester) is attached to another ring structure in a spiro configuration (i.e., the lactone ring shares a single carbon atom with the other ring). Spirolactones which are coupled to steroids are the most important class of spirolactones from a pharmaceutical perspective, so they are widely referred to in the pharmaceutical arts simply as spirolactones. As used herein, "spirolactone" refers to a molecule comprising a lactone structure coupled via a spiro configuration to a steroid structure or steroid derivative.

One particular spirolactone which functions as an effective ALDO antagonist is called spironolactone, which is marketed as an anti-hypertensive and diuretic drug by G.D. Searle (Skokie, Ill.) under the trademarks "Aldactone" and "Aldactazide." Spironolactone is the name commonly used by chemists; the full chemical name is 17-hydroxy-7-alpha-mercapto-3-oxo-17-alpha-pregn-4-ene-21-carboxylic acid gamma-lactone acetate. This compound, its activities, and modes of synthesis and purification are described in a number of U.S. Pat. Nos. including 3,013,012 (Cella and Tweit 1961) and 4,529,811 (Hill and Erickson 1985).

Spironolactone functions as an antagonist of ALDO; it occupies ALDO receptors without triggering the normal receptor activity. This competitive binding reaction reduces the ability of ALDO molecules to bind to and trigger activity at such receptors. As used herein, "aldosterone antagonist" refers to a compound that suppresses the receptor-mediated activity of aldosterone; it does not include compounds which reduce the amount of aldosterone synthesized or secreted by the adrenal cortex, such as mespirenone (discussed below).

When spironolactone is used to suppress ALDO activity, it promotes the elimination of fluid and sodium by the body, primarily via the kidneys and its formation of urine. Both of these effects help control hypertension in people suffering from high blood pressure. Spironolactone is therefore used to treat hypertension. The minimum effective anti-hypertensive dosage in adults is about 50 milligrams (mg) per day; dosages often exceed this, and dosages of 200 to 400 mg/day are common for chronic treatment. Since spironolactone is metabolized and secreted fairly rapidly, typical administration involves pills containing 25 to 100 mg, taken four times daily.

The anti-hypertensive dosage of spironolactone is important to the subject invention, because it has been discovered that spironolactone can be used for an entirely different purpose (to inhibit fibrosis, as described herein) at dosages that are below the dosages which have anti-hypertensive effects. This is a useful finding, since it indicates that spirolactones can be used to prevent unwanted fibrosis at dosages which have minimal side effects and do not substantially alter the body fluids or mineral concentrations of a patient.

As mentioned above, ALDO is secreted as one step in a multi-step pathway involving renin and angiotensin, in the RAA system. Various drugs have been identified which can inhibit one or more of the steps in this pathway. For example, if a drug classified as an "ACE inhibitor" (i.e., it inhibits angiotensin converting enzyme) is used to suppress the formation of angiotensin II, secretion of ALDO by the adrenal cortex will be suppressed. The most widely used ACE inhibitor is captopril.

In addition, certain drugs have been identified which appear to block ALDO synthesis and/or secretion by a more direct mechanism. These drugs include 15,16-methylene spirolactone compounds called Mespirenone (also called ZK 94679) and dethiolated Mespirenone (also called ZK 91587); see Losert et al 1986, Nickisch et al 1991, and Agarwal and Lazar 1991.

One object of this invention is to disclose a method of using an aldosterone antagonist, at a dosage which does not disrupt a patient's normal electrolyte and water-retention balance, to treat or prevent myocardial fibrosis. This and other objects will become more apparent in the following summary and description.

SUMMARY OF THE INVENTION

This invention discloses a method of using an aldosterone antagonist such as spironolactone, at a dosage which does not disrupt a patient's normal electrolyte and water-retention balance, to inhibit myocardial fibrosis, including left ventricular hypertrophy (LVH).

DESCRIPTION OF THE PREFERRED EMBODIMENTS

This invention discloses a method of using an aldosterone antagonist such as spironolactone, at a dosage which does not disrupt a patient's normal electrolyte and water-retention balance, to prevent or otherwise inhibit myocardial fibrosis. As discussed herein, disruption of a patient's normal electrolyte balance refers to a substantial alteration of sodium or potassium concentrations in the patient's blood. At the dosages used to treat hypertension (high blood pressure) or edema (excessive fluid accumulation in the body), spironolactone substantially reduces sodium levels and increases potassium levels in the body. These alterations in the homeostatic mineral balances of the body can provoke a number of unpleasant side effects; accordingly, use of lower dosages to inhibit myocardial fibrosis can avoid or minimize such side effects.

As used herein, "treatment" or "inhibition" of myocardial fibrosis are used interchangeably to include (1) treatment of patients in which myocardial fibrosis has already reached dangerous or damaging levels, and (2) preventive or prophylactic treatment of patients who are at high risk of myocardial fibrosis, or who are displaying symptoms that suggest the possible approach or onset of myocardial fibrosis.

Patients can exhibit indications of myocardial fibrosis in any of several ways, including symptoms reported by the patients (such as shortness of breath), signs which are observed by a physician (such as pleural effusion, which involves fluid in the chest), and through the results of laboratory analyses (such as blood gas abnormalities, or abnormal appearances on an echocardiogram). If a physician or pathologist determines that myocardial fibrosis is occurring or poses a serious threat in a specific patient, the physician can prescribe an aldosterone antagonist such as a spirolactone to inhibit the fibrosis.

An important aspect of this invention is that the treatment can utilize a low dosage of the aldosterone antagonist. As described in Example 2, tests have indicated that spironolactone is effective in preventing myocardial fibrosis at dosages which are below anti-hypertensive dosages. This allows anti-fibrotic administration of an aldosterone antagonist at dosages which have minimal side effects and do not substantially disrupt electrolyte balances or water retention in the patient.

The evidence which shows that ALDO is a primary and direct causative agent which induces myocardial fibrosis is contained in Examples 1 through 3. Example 1 describes three different techniques that were used to create hypertension in rats:

(1) in some rats, renovascular hypertension (RHT) was induced by surgically placing a constricting band around the right renal artery, to induce unilateral renal ischemia. This method is described in Doering et al 1988. The right kidney, in response to the apparent low blood pressure, releases renin, which activates the renin-angiotensin-aldosterone (RAA) system. This hormonal complex results in increased blood pressure, increased angiotensin II concentrations, and increased ALDO concentrations.

(2) infrarenal banding (IRB) was used in other rats. This involves constricting flow through the aorta, below the junction where the renal arteries (which supply the kidneys) branch off from the abdominal aorta. This reduces blood flow to the legs, and it elevates blood pressures in the kidneys and other internal organs, excluding the lungs (which are served by the right ventricle). Despite the rise in blood pressure, concentrations of circulating angiotensin II and ALDO remain relatively normal in this treatment.

(3) in other rats, direct infusion of ALDO was used, via osmotic minipumps. These pumps do not use moving parts; instead, they act by causing a solution to diffuse out of the pump through a membrane, driven by osmotic pressure. These pumps, loaded with ALDO, were implanted subcutaneously in uni-nephrectomized rats (i.e., rats from which one kidney had been removed), and they released ALDO directly into the circulating blood. After ALDO levels increased, due to this direct ("primary") infusion, the levels of angiotensin II typically decreased during the first four weeks, then gradually returned to normal levels.

These treatments lasted 8 weeks; during this time, all three treatment groups showed comparable levels of elevated blood pressure. The animals were then sacrificed and the hearts were dissected and analyzed. All three groups showed comparable levels of left ventricular hypertrophy. However, increased collagen formation (indicating unwanted fibrosis) was found only in rats with renovascular hypertension (which causes elevated concentrations of both angiotensin II and ALDO) and in rats receiving ALDO by minipump. The rats that were treated with infrarenal banding (with normal levels of angiotensin II and ALDO) developed left ventricular hypertrophy, but they did not suffer a fibrotic response.

These findings indicated that myocardial fibrosis involved a cellular mechanism that did not depend solely on the presence of hypertension, which apparently was mediated by some combination of angiotensin II and/or aldosterone. These results, which were reported in Doering et al 1988 and Brilla et al 1990, began the process of identifying the role of mineralocorticoids in promoting fibrosis, but they did not adequately resolve a number of questions, such as questions relating to the respective contributions of those two hormones. To further resolve those and other issues, additional tests were done involving (1) the in vivo use of captopril, an ACE inhibitor which suppresses the synthesis of angiotensin II, and (2) in vitro tests involving cultured fibroblast cells.

The tests involving captopril are described in Example 2. Briefly, rats were subjected to either of two treatments: (1) direct injection of ALDO coupled with a high salt diet, in uni-nephrectomized rats, or (2) unilateral renal ischemia, to induce renovascular hypertension (RHT). These two treatments can be regarded as primary ALDO elevation (i.e., direct injection of ALDO), or secondary ALDO elevation (due to RHT treatment, which increases ALDO levels as one step in the RAA hormonal cascade).

Each treatment group (primary or secondary) was divided into four subgroups which received different treatments over an eight week period, as follows:

(1) One pair of subgroups received an ACE inhibitor, captopril, to suppress the synthesis of angiotensin-II in those with secondary ALDO elevation;

(2) One pair of subgroups received a low dose of spironolactone, an ALDO antagonist. Under the conditions used, this dosage was not high enough to suppress hypertension in animals with primary ALDO elevation.

(3) One pair of subgroups received a high dose of spironolactone, sufficient to suppress hypertension in animals with primary ALDO elevation.

(4) The control subgroups did not receive any treatment, other than the treatments which induced primary or secondary ALDO elevation.

The results were as follows:

(1) Captopril treatment, which inhibited the formation of angiotensin-II, prevented hypertension in both subgroups. It also prevented secondary hyperaldosteronism and fibrosis in rats with induced RHT. However, it did not prevent fibrosis in rats treated directly with ALDO infusion.

(2) The high dose of spironolactone prevented hypertension, LVH, and fibrosis. The small dose of spironolactone was not able to prevent either hypertension or LVH, but it was able to prevent fibrosis.

These findings indicated that ALDO, rather than angiotensin or arterial hypertension, is a primary and direct causative agent of fibrosis. They also indicated that fibrosis can be blocked by suppressing activity at ALDO receptors, using an ALDO antagonist such as spironolactone, at a dosage below the dosage required to suppress hypertension.

In the in vitro tests described in Example 3, cardiac fibroblast cells were harvested from rats, separated from each other using collagenase, and divided into different treatment groups. One group of cells was incubated with aldosterone. A second group of cells was incubated with dexamethasone, a glucocorticoid that inhibits collagen synthesis. A third group was incubated with a mixture of aldosterone and spironolactone, and a fourth (control) group was not treated with any exogenous gluco- or mineralocorticoids. During a 24-hour incubation period, the nutrient medium contained proline (an amino acid) which was radio-labelled with tritium [$^3$H]. Since proline is present at high concentrations in collagen, $^3$H-proline incorporation into insoluble protein during the incubation period provided an indicator of collagen synthesis.

At the end of the incubation period, cells were lysed and insoluble proteins were purified using chemical processing followed by centrifugation. The pelleted proteins were resuspended and then digested with collagenase, to solubilize collagen and its amino acids. The mixture was pelleted again and then analyzed to determine the concentration of solubilized labelled protein in the supernatant. This quantity was divided by the total labelled proline content in both the pellet and the supernatant, to provide a numerical index of collagen formation.

The results, shown in Table 1 (in Example 3), indicate that ALDO caused a marked increase in collagen synthesis in cardiac tissue.

Oral Dosages and Reduction of Side Effects

Spironolactone is sold in 25, 50 or 100 mg tablets, which are taken orally for edema or hypertension. It is sold by G.D. Searle and Company (Skokie, Ill.) under the trademarks Aldactone (containing spironolactone as the sole active ingredient) and Aldactazide (which contains spironolactone combined with hydrochlorothiazide, a diuretic).

The *Physician's Desk Reference* (PDR) makes a number of pertinent comments about dosages for spironolactone when treating edema, hypertension, For "essential hypertension" in adults, initial dosages of 50 to 100 mg are recommended; for edema (including congestive heart failure, hepatic cirrhosis, and nephrotic syndrome) initial dosages 100 are recommended. In either situation the patient should be monitored and the dosage should be adjusted, depending on how the patient responds, to a range of 25 to 100 mg (or more). For a somewhat different condition called hypokalemia (potassium deficiency, usually induced by treatment with a diuretic), dosages of 25 to 100 mg are also recommended.

These recommended dosages must be viewed in light of warnings in the PDR about the risks and unwanted side effects of spironolactone. It has been shown to be a tumorigen (cancer-causing agent) in chronic toxicity studies; in addition, "Carcinoma of the breast has been reported in patients taking spironolactone, but a cause and effect relationship has not been established."

In addition to possibly increasing the risk of cancer, spironolactone causes major disruptions in the balance of minerals within the body. These disruptions can create or aggravate any number of unpleasant symptoms that are given labels such as hyperkalemia, hyperchloremic metabolic acidosis, hyponatremia, gynecomastia, and agranulocytosis. In addition, as stated in the PDR, "Other adverse reactions that have been reported in association with [spironolactone] are: gastrointestinal symptoms including cramping and diarrhea, drowsiness, lethargy, headache, maculopapular or erythematous cutaneous eruptions [i.e., spontaneous or excessive bleeding], urticaria [i.e., intense itching], mental confusion, drug fever, ataxia [i.e., loss of muscle coordination], inability to achieve or maintain erection, irregular menses [menstruation] or amenorrhea, postmenopausal bleeding, hirsutism [i.e., abnormal hair growth], deepening of the voice, gastric bleeding, ulceration, gastritis, and vomiting."

Any one of the above-listed side effects can make life miserable for a patient who must endure it. The fact that all of these side effects have been associated with spironolactone indicates that it can have unpleasant side effects, and it should be taken only when necessary and at the lowest dosage that can achieve the necessary result.

The risks, rates of occurrence, and severity of these noxious side effects will be substantially reduced if the dosages of spironolactone can be reduced. Due to a number of factors, even a modest reduction in dosage can completely eliminate or greatly reduce such side effects in many people. Therefore, the discovery that spironolactone is effective against myocardial fibrosis, at dosages lower than necessary for controlling hypertension, is an important discovery and an important feature of this invention.

In accord with this teaching, this invention discloses oral tablets or capsules containing from 10 to 20 mg of spironolactone. In view of the noxious side effects of spironolactone, the difference between this dosage range and the smallest dosages currently available (25 mg) is substantial, and will provide a major benefit to many users.

Spironolactone is discussed herein because it is an archetypical ALDO antagonist, which selectively and specifically blocks ALDO receptors. If desired, other ALDO antagonists could be used instead of spironolactone, either to block the activity of ALDO molecules at ALDO receptors, or to suppress the biosynthesis of ALDO at the adrenal cortex. Since the activation of ALDO receptors by ALDO molecules has been shown to be a key step in the chain of events leading to myocardial fibrosis, any ALDO antagonist which can block or inhibit that ALDO/receptor interaction will effectively break that chain and stop the cascade of events leading to myocardial fibrosis.

EXAMPLES

Example 1

In Vivo Studies Involving Chronic Hypertension

Arterial hypertension was induced in eight week old male Sprague Dawley rats (180–200 g), using three different techniques:

(1) in some animals, renovascular hypertension (RHT) was induced by surgically placing a constricting band around the right renal artery, to induce unilateral renal ischemia.

(2) in other animals, infrarenal banding (IRB) was used to mechanically constrict blood flow through the aorta below the junction where the renal arteries branch off. This elevates blood pressures in the kidneys, but angiotensin II and ALDO remain relatively normal.

(3) ALDO (d-aldosterone, purchased from Sigma Chemical, St. Louis, Mo.) was directly infused into the animals at the rate of 0.75 micrograms (ug) per hour, via osmotic minipumps (Alzet Model 2002), Alza Corp., Palo Alto, Calif.) which were implanted subcutaneously in uninephrectomized rats. These rats were fed standard rat chow with a sodium concentration of 0.4% and additional sodium in the drinking water (10 g/L) resulting in a high sodium diet. ALDO levels were elevated due to the direct ("primary") infusion. Angiotensin II levels typically decreased (to about 10–15 picograms per ml of blood) during the first four weeks, then gradually rose to normal levels (about 30 pg/ml).

Control animals were (1) uninephrectomized rats on a high sodium diet with implanted minipumps, but where aldosterone administration was withheld, and (2) unoperated, untreated, age and sex matched controls.

These treatments lasted for 8 weeks. During this period, the rats were monitored for hypertension, using a tail cuff. All three treatment groups suffered comparable levels of hypertension (in the range of about 190–200 mm Hg) compared to blood pressures of about 130–140 in control animals. Plasma aldosterone was measured using a radioimmunoassay (Diagnostic Products Corp., Los Angeles, Calif.) with sample aldosterone competing with $^{125}$I-radiolabeled aldosterone for antibody sites. Urine sodium and potassium concentrations were measured by flame photometry.

At the end of the 8 week treatment, the rats were sacrificed, and the hearts were dissected and analyzed. Coronal sections were dehydrated and embedded in paraffin. The weights of the left ventricles were determined and compared to right ventricle weight and total body weight; Thereafter, sections which were 5 microns thick, containing a complete cross sectional cut of the left ventricle, were stained with the collagen specific dye Sirius Red F3BA (Pfaltz & Bauer, Stamford Conn.). Connective tissue and muscle areas were identified according to their gray level, where collagen fibers appear black, myocytes are gray, and interstitial space is white. Digitized profiles were created using an automated image analyzer (Quantimet 520, Cambridge Instruments, Inc., Deerfield, Ill.) and transferred to a computer that calculated collagen volume fraction as the sum of all connective tissue areas in the entire section, divided by the sum of all connective tissue and muscle areas. Perivascular collagen was excluded from this analysis and was measured separately. Total collagen volume fraction (including all perivascular collagen), as determined by this morphometric approach, is closely related to hydroxyproline concentration of the left ventricle.

Similarly, perivascular collagen area (PVCA) normalized to vessel luminal area of intramural coronary arteries was determined in Sirius Red stained tissue using the automated image analyzer. Only those intramyocardial vessels which appeared circular on cross section were analyzed to ensure correct normalization for vessel luminal area; on the average there were 15 such vessels found in the left ventricle. The investigator responsible for the morphometric analysis was blinded as to each experimental group.

Interstitial collagen volume fraction (CVF) was determined using picrosirius stained tissue.

All three treatment groups showed comparable levels of arterial hypertension and left ventricular hypertrophy. However, increased CVF indicating fibrosis was found only in rats with renovascular hypertension (RHT), which causes elevated concentrations of both angiotensin II and ALDO, and rats receiving ALDO by minipump. The rats that were treated with infrarenal banding (with normal levels of angiotensin II and ALDO) suffered left ventricular hypertrophy, but they did not suffer a fibrotic response. This finding indicated that cardiac fibrosis apparently involved a cellular mechanism that did not depend solely on the presence of hypertension, which apparently was mediated by some combination of angiotensin II and/or aldosterone.

Example 2

Studies Involving Inhibition of Angiotensin II

Rats were treated to generate primary hyperaldosteronism (by directly injecting ALDO in uninephrectomized rats) or secondary hyperaldosteronism (by creating unilateral renal ischemia, which induced RHT as above) using the same procedures described in Example 2. Each treated group was divided into four subgroups which received different treatment over an eight week period, as follows:

(1) One pair of subgroups received an ACE inhibitor, captopril, to suppress the synthesis of angiotensin-II.

(2) One pair of subgroups received a relatively low dose (20 mg/kg/day) of the ALDO antagonist, spironolactone. This dosage was not sufficient to suppress hypertension.

(3) One pair of subgroups received a higher quantity (200 mg/kg/day) of spironolactone, which is sufficient to suppress hypertension.

(4) The control subgroups did not receive any treatment, other than the treatments which induced primary or secondary ALDO elevation.

The results were as follows:

(1) Captopril treatment, which inhibited the formation of angiotensin-II, prevented hypertension in both subgroups. It also prevented the induction of secondary hyperaldosteronism, and the induction of fibrosis, in rats with induced RHT. However, it did not prevent fibrosis in rats that were treated directly with ALDO injections.

(2) The large dose of spironolactone prevented hypertension, LVH, and fibrosis. The small dose of spironolactone was not able to prevent either hypertension or LVH, but it was able to prevent fibrosis.

These findings indicated that ALDO, rather than angiotensin or arterial hypertension, is the primary and direct causative agent of fibrosis. They also indicate that fibrosis can be blocked by suppressing activity at ALDO receptors, using spironolactone.

Example 3

In Vitro Studies of Fibroblasts

Cardiac fibroblast cells were harvested from rats, separated by digestion with collagenase, and divided into different treatment groups which were cultured in nutrient medium supplemented with fetal calf serum. One group was incubated with $10^{-9}$ M aldosterone; another group was incubated with $10^{-9}$ M dexamethasone, a glucocorticoid which inhibits collagen synthesis. A third group was incubated with a mixture of $10^{-9}$ M aldosterone and $10^{-6}$ M spironolactone. A fourth (control) group was not treated with any exogenous gluco- or mineralocorticoids.

During the 24-hour incubation period, the nutrient medium contained proline which was radiolabelled with tritium [$^3$H]. Since proline is present at high concentrations in collagen, $^3$H-proline incorporation into insoluble protein during the incubation period provided an indicator of collagen synthesis (CS). At the end of the incubation period, the cells were lysed and insoluble proteins were purified using chemical processing followed by centrifugation. The pelleted proteins were resuspended and then digested with collagenase, to solubilize the collagen. The mixture was pelleted again and then analyzed to determine the concentration of solubilized labelled protein in the supernatant. This quantity was divided by the total labelled proline content in both the pellet and the supernatant, to provide a numerical index of collagen formation. This number has been shown to correlate well with the digital optical analysis of stained tissue described in Example 1.

Cell counts were estimated visually on a number per square centimeter basis; since they are anchorage dependent, they cannot be analyzed easily using flow cytometry. DNA synthesis was analyzed using radiolabelled thymidine and an intercalating dye, Fluorochrome H33258 (Calbiochem, La Jolla, Calif.).

The results, shown in Table 1, indicate that ALDO caused a marked increase in collagen synthesis.

TABLE 1

| Treatment | C#/$10^5$ | CS/cell | CS/DNA | CS/protein |
| --- | --- | --- | --- | --- |
| ALDO | 2.3 ± 0.4 | 16.1 ± 3.9 | 3.3 ± 0.7 | 5.9 ± 1.0 |
| DEXA | 2.4 ± 0.5 | 1.6 ± 0.7 | 0.4 ± 0.2 | 1.5 ± 0.8 |
| ALDO + SL | 1.9 ± 0.5 | 18.2 ± 4.2 | 2.9 ± 0.2 | 6.1 ± 0.8 |
| Control | 2.1 ± 0.3 | 5.6 ± 2.2 | 0.8 ± 0.2 | 2.9 ± 0.5 |

Thus there has been shown and described a method and a composition for using aldosterone antagonists to suppress undesired myocardial fibrosis, at a dosage below the level required to suppress hypertension. This disclosure is set forth in certain specific embodiments, but it will be apparent to those skilled in the art that various changes and modifications to the specific embodiments described herein are possible. Any such changes that do not depart from the spirit and scope of the invention are deemed to be covered by the invention, which is limited only by the claims which follow.

REFERENCES

Agarwal, M. K. and Lazar, G., "Antimineralocorticoids," *Renal Physiol. Biochem.* 14:217–223 (1991)

Barton, D. H. R., et al, *J. Chem. Soc. Perkin Trans I*: 2243 (1975)

Blitstein-Willinger, E., "The role of growth factors in wound healing," *Skin Pharmacol.* 4:175–182 (1991)

Brilla, C. G., et al, "Remodeling of the rat right and left ventricle in experimental hypertension," *Circ. Res.* 67:1355–1364 (1990)

Doering, C. W., et al, "Collagen network remodeling and diastolic stiffness of the rat left ventricle with pressure overload hypertrophy," *Cardiovasc. Res.* 22:686–695 (1988)

Hassager, C., et al, "Collagen synthesis in postmenopausal women during therapy with anabolic steroid or female sex hormones," *Metabolism* 39:1167–1169 (1990)

Jalil, J. E., et al, "Structural vs. contractile protein remodeling and myocardial stiffness in hypertrophied rat left ventricle," *J. Mol. Cell Cardiol* 20:1179–1187 (1988)

Jalil, J. E., et al, "Fibrillar collagen and myocardial stiffness in the intact hypertrophied rat left ventricle," *Circ. Res.* 64:1041–1050 (1989)

Kornel, L., et al, "Arterial steroid receptors and their putative role in the mechanism of hypertension," *J. Steroid Biochem.* 19:333–344 (1983)

Losert, W. et al, "Mespirenone and other 15,16-methylene-17-spirolactones, a new type of steroidal aldosterone antagonists," *Drug Res.* 36:1583–1600 (1986)

Luke, J. L., et al, "Sudden cardiac death during exercise in a weight lifter using anabolic steroids: Pathological and toxicological findings," *J. Forensic Sci.* 35:1441–1447

Meyer, W. J., and Nichols, N. R., "Mineralocorticoid binding in cultured smooth muscle cells and fibroblasts from rat aorta," *J. Steroid Biochem.* 14:1157–1168 (1981)

Miyano, M., *J. Org. Chem.* 46:1846 (1981)

Nickische, K., et al, "Aldosterone Antagonists," *J. Med. Chem.* 34:2464–2468 (1991)

Rothe, M., and Falanga, V., "Growth factors: Their biology and promise in dermatologic diseases and tissue repair," *Arch. Dermatol.* 125:1390–1398 (1989)

Skelton, F. R., "The production of hypertension, nephrosclerosis and cardiac lesions by methylandrostenediol treatment in the rat," *Endocrinology* 53:492–505 (1954)

Weber, K. T., and Brilla, C. G., "Pathological hypertrophy and cardiac interstitium," *Circulation* 83:1849–1865 (June 1991)

What is claimed is:

1. A method of inhibiting aldosterone-mediated myocardial fibrosis, comprising administering to a patient in need thereof an aldosterone antagonist which suppresses activity at aldosterone receptors in a mammalian body, wherein said aldosterone antagonist is administered in a quantity that is therapeutically effective in suppressing aldosterone-mediated myocardial fibrosis without substantially disrupting the water-retention balance of the body.

2. The method as recited in claim 1 wherein the aldosterone antagonist which suppresses activity at aldosterone receptors comprises a spirolactone compound having a lactone ring coupled to a steroid structure in a spiro configuration.

3. The method recited in claim 2 wherein the spirolactone compound comprises spironolactone.

4. The method recited in claim 1 wherein an oral tablet or capsule comprising between 10 and 20 milligrams spironolactone is administered to an adult patient.

5. A method of inhibiting aldosterone-mediated myocardial fibrosis in a patient at risk of myocardial fibrosis, comprising administering to a patient in need thereof an aldosterone antagonist which suppresses activity at aldosterone receptors in a mammalian body, wherein said aldosterone antagonist is administered in a quantity that is therapeutically effective in suppressing aldosterone-mediated myocardial fibrosis without substantially increasing sodium excretion by the body.

6. The method as recited in claim 1 wherein the aldosterone antagonist which suppresses activity at aldosterone receptors comprises a spirolactone compound having a lactone ring coupled to a steroid structure in a spiro configuration.

7. The method recited in claim 2 wherein the spirolactone compound comprises spironolactone.

8. The method recited in claim 1 wherein an oral tablet or capsule comprising between 10 and 20 milligrams spironolactone is administered to an adult patient.

9. A method of inhibiting aldosterone-mediated deposition of pathological concentrations of collagen, comprising administering to a patient in need thereof an aldosterone antagonist which suppresses activity at aldosterone receptors in a mammalian body, wherein said aldosterone antagonist is administered in a quantity that is therapeutically effective in suppressing aldosterone-mediated deposition of pathological concentrations of collagen without substantially increasing sodium excretion by the body.

10. The method as recited in claim 5 wherein the aldosterone antagonist which suppresses activity at aldosterone receptors comprises a spirolactone compound having a lactone ring coupled to a steroid structure in a spiro configuration.

11. The method recited in claim 6 wherein the spirolactone compound comprises spironolactone.

12. The method recited in claim 5 wherein an oral tablet or capsule comprising between 10 and 20 milligrams spironolactone is administered to an adult patient.

13. A method of inhibiting aldosterone-mediated reactive fibrosis, comprising administering to a patient in need thereof an aldosterone antagonist which suppresses activity at aldosterone receptors in a mammalian body, wherein said aldosterone antagonist is administered in a quantity that is therapeutically effective in suppressing reactive fibrosis without substantially increasing sodium excretion by the body.

14. The method as recited in claim 9 wherein the aldosterone antagonist which suppresses activity at aldosterone receptors comprises a spirolactone compound having a lactone ring coupled to a steroid structure in a spiro configuration.

15. The method recited in claim 10 wherein the spirolactone compound comprises spironolactone.

16. The method recited in claim 9 wherein an oral tablet or capsule comprising between 10 and 20 milligrams spironolactone is administered to an adult patient.

17. A method of inhibiting aldosterone-mediated perivascular fibrosis, comprising administering to a patient in need thereof an aldosterone antagonist which suppresses activity at aldosterone receptors in a mammalian body, wherein said aldosterone antagonist is administered in a quantity that is therapeutically effective in suppressing perivascular fibrosis without substantially increasing sodium excretion by the body.

18. The method as recited in claim 13 wherein the aldosterone antagonist which suppresses activity at aldosterone receptors comprises a spirolactone compound having a lactone ring coupled to a steroid structure in a spiro configuration.

19. The method recited in claim 14 wherein the spirolactone compound comprises spironolactone.

20. The method recited in claim 13 wherein an oral tablet or capsule comprising between 10 and 20 milligrams spironolactone is administered to an adult patient.

* * * * *